United States Patent [19]
Nowak

[11] Patent Number: 5,997,298
[45] Date of Patent: Dec. 7, 1999

[54] ORAL SURGICAL INSTRUMENT (OSTEOTOME) AND METHOD FOR CREATING OPENINGS IN THE JAWBONE FOR IMPLANTS

[75] Inventor: Marcus Nowak, Berlin, Germany

[73] Assignee: Friadent GmbH, Germany

[21] Appl. No.: 08/831,092

[22] Filed: Apr. 1, 1997

[30] Foreign Application Priority Data

Apr. 1, 1996 [DE] Germany ............................ 196 13 743

[51] Int. Cl.⁶ .................................................. A61C 3/02
[52] U.S. Cl. ............................ 433/165; 433/75; 433/173
[58] Field of Search .................................. 433/165, 166, 433/173, 75

[56] References Cited

U.S. PATENT DOCUMENTS

| | | | |
|---|---|---|---|
| 1,366,877 | 1/1921 | Craig | 433/75 |
| 4,185,383 | 1/1980 | Heimke et al. | 433/173 |
| 4,474,556 | 10/1984 | Ellis et al. | 433/173 |
| 4,475,890 | 10/1984 | Heidelbach | 433/173 |
| 4,998,881 | 3/1991 | Lauks | 433/75 |
| 5,199,873 | 4/1993 | Schulte et al. | 433/173 |
| 5,261,818 | 11/1993 | Shaw | 433/166 |

FOREIGN PATENT DOCUMENTS

| | | |
|---|---|---|
| 26 19 650 B2 | 9/1980 | Germany . |
| 43 16 955 A1 | 5/1994 | Germany . |
| WO 95/21590 | 8/1995 | WIPO . |

*Primary Examiner*—John J. Wilson
*Attorney, Agent, or Firm*—McGlew and Tuttle, PC.

[57] ABSTRACT

An oral surgical instrument (osteotome) for creating openings in the jawbone for the implantation of implants, which comprises a holder, a shaft and a working tip that has a circular cross section. A set of surgical instruments is provided with at least one preformer having a conical working tip and at least one implant bed former having a working tip which is adapted to the outer contour of the implant. The diameter of the working tip of the preformer is somewhat smaller than the largest diameter of the working tip of the implant bed former. By forming the openings in the jawbone using such instruments, the implants may be inserted with a greater fitting strength.

19 Claims, 6 Drawing Sheets

ORAL SURGICAL INSTRUMENT (OSTEOTOME) AND METHOD FOR CREATING OPENINGS IN THE JAWBONE FOR IMPLANTS

FIELD OF THE INVENTION

The present invention pertains to an oral surgical instrument (osteotome) for creating openings in the jawbone for the implantation of implants. It is a styloid instrument and comprises a holder, a shaft, and a working tip that has a circular cross section.

BACKGROUND OF THE INVENTION

An oral surgical instrument (osteotome) of a generic type is known from DE 43 16 955 A1. This instrument is used for the surgical splitting and spreading of sections of the jaw for the implantation of implants that have a circular cross section, especially in the upper jaw. The drawback in this case is a relatively great length of the osteotomy line because of the slot shape of the opening that is created in the jaw. This frequently leads to postoperative loosening of the implant or to a poor healing of the wound. This is supposed to be avoided with the better working tip of the anticipated dental instrument, which can be adapted to the jaw ridge, but a relatively high operating expense is necessary when using the anticipated dental instrument in order to implant an implant for the fixation of tooth crowns.

On the other hand, the creation of jaw openings for the implantation of implants by means of drilling is well known in dentistry. As a result of this, however, valuable bone material is removed, due to which the fitting strength of the implant is not guaranteed. It is well known in dentistry that the bone material of the upper jaw is considerably softer than the bone material of the lower jaw, whereby the bone material of the upper jaw may be compared with balsa wood in terms of its strength. The bone material is divided into a plurality of bone classes, whereby even osteoporosis, i.e., the structural change of the bone material in old age, is taken into consideration. Especially with regard to the softness of the bone material of the upper jaw, the drilling for the formation of openings in the upper jaw for the implantation of implants proves to be extremely unfavorable, since bone material is still removed from the soft bone material anyway.

An instrument (osteotome) according to Summers, which comprises a handle-like holder and a shaft with a working tip having a circular cross section, and which is provided with graduated rings on its shaft that are directly connected to the working tip and with a concave spherical cap on its end, has previously become known especially for the formation of openings in the upper jaw for the implantation of implants. Summers' osteotomes have the shape of a graduated round rod. They are available in six sizes with increasing diameters. In each case, the next largest instrument is inserted into the jaw opening formed. The implant bed is created by means of expanding and compressing the bone material. The working end of the instruments is concave and is bordered with sharp edges. The penetration depth of the instruments is determined by means of markings. By pressing in the dental instrument to form the opening, the bone material of the upper jaw is displaced and compacted. The bone material expands after pulling out the dental instrument and after implanting the implant and it holds onto this. In the ensuing time, new bone material is formed around the implanted implant. Thus, no bone material is removed in this method of implantation, but the bone material, especially of the soft upper jaw, is, in contrast, absolutely compacted. However, the drawback thereby is the formation of simple, slightly conical cavities in the jaw, especially in the upper jaw, which do not guarantee a reliable bed for the fixation especially of screw-type implants. Especially since prior-art implants have different outer contours, e.g., graduated cylinder implants with and without screw threads, as well as cylinder implants with and without partial or continuous screw threads, the conventional, slightly conical, oral surgical instruments according to Summers are unable to guarantee that the slightly conical opening formed in the jaw will reliably hold the implanted implant.

SUMMARY AND OBJECTS OF THE INVENTION

Therefore, the primary object of the present invention is to create an oral surgical instrument (osteotome) of the generic type, with which openings in the jaw, especially in the upper jaw, can be formed for implanting implants, so that these implants can be inserted into the openings in the jaw with greater fitting strength.

The object is accomplished by an oral surgical instrument (osteotome) for creating openings in the jawbone for the implantation of implants, which is characterized by a set of dental instruments, comprising at least one preformer having a conical working tip and at least one implant bed former with a working tip adapted to the outer contour of the implant, whereby the diameter of the working tip of the preformer is somewhat smaller than the largest diameter of the working tip of the implant bed former. According to the present invention, first a smaller opening is created in the jaw, especially in the upper jaw, with the preformer having a conical working tip by means of the lateral pushing away of the bone material of the jaw, which opening is still not sufficient to insert the implant to be implanted. The bone material of the jaw, especially of the upper jaw is first further displaced by the implant bed former according to the present invention with a working tip that is adapted to the outer contour of the implant, whose diameter is somewhat greater than the largest diameter of the working tip of the preformer, to the extent that the opening created in the jaw is already adapted to the outer contour of the implant. This implant can then be pressed into or screwed into the opening thus created in the jaw, especially in the upper jaw, whereby the implant is held firmly by the bone material of the jaw, especially the upper jaw, which expands again after pulling out the implant bed former and after implantation of the implant. The new bone material that forms around the implant in the ensuing time then holds the implant firmly in the jaw opening that has been adapted to its outer contour in an optimal manner. According to the present invention, the specific shape of the implant is already taken into account during the initial shaping of the implant bed of the jaw opening in the bone material, since the shape of the implant in the jaw opening is created exactly with the implant bed last used. Thus, even implants having a graduated contour may be used. Rotating instruments were previously necessary for this type of implant bed.

For the implantation of an implant having a graduated diameter in the form of a graduated cylinder or graduated screw, the working tip of the implant bed former has an outer contour with a graduated diameter on its free end, which outer contour is adapted to the outer contour of the graduated cylinder, i.e., it corresponds to this contour, whereby, in a graduated screw, the respective inner diameter of the graduated implant is drawn closer for the formation of the shape of the working tip of the implant bed former. In another variant of the present invention, the conical contour lines of the working tip of the preformer in this embodiment are designed in that they run through the inner edges of the graduations of the graduated contour lines of the working tip of the implant bed former, which project onto the working tip of the implant bed former. Thus, the jaw opening is already preformed with the preformer to the extent that only the graduation areas for the implantation of the graduated cylinder or of the graduated screw as the implant must still be formed with the graduated working tip of the implant bed former. In another variant of this embodiment, the front end of the conical working tip of the preformer is designed as a concave cavity, so that the bone material of the jaw, especially of the upper jaw is cut, on the one hand, by means of the marginal edges of the front end of the working tip as the preformer is pressed in, and on the other hand, is entrained by means of the concave recess of the working tip and is deposited and compressed at the end of the pressing in of the preformer. Furthermore, bone replacement material—if necessary—is also moved with the concave working tip of the preformer. The front end of the working tip of the implant bed former is shaped like a pointed cone, especially less than 120°0, in order to guarantee a slight penetration of the graduated implant bed former into the jaw opening formed by the preformer.

In another embodiment of the present invention, the working tip of the implant bed former has a conical outer contour for the formation of a jaw opening for a cylindrical implant, whereby the cone angle of the implant bed former is somewhat greater than the cone angle of the preformer. This also results in a thickening of the bone material laterally to the jaw opening when the conical preformer is inserted. Cylindrical implants with complete, partial or no threads can be reliably implanted into the slightly conical jaw opening thus formed. In this embodiment, the front end of the working tip of the implant bed former is designed as a concave cavity, whereas the front end of the working tip of the preformer is shaped like a pointed cone, especially less than a cone angle of about 120°.

Further, in still another embodiment of the present invention, the shaft area, which is directly connected to the working tips of the preformer and the implant bed former, is provided with at least one circumferential notch as a depth scale. This depth scale makes it possible for the operator to control the penetration depth of the preformer and of the implant bed former with the highest precision in order to adapt the preformer and implant bed former to the length of the implant to be implanted. In a preferred embodiment, the shaft area of the preformer and implant bed former has a plurality of notches, which are arranged at a distance from one another, as a depth scale.

When screw-type implants are inserted into the slightly conical cavity formed by means of the instrument (osteotome) according to Summers, there is the risk that uncontrolled breaks and splittings may occur in the bone, which is now thickened and no longer so elastic. By not adequately considering the specific shape of the implant, the filigree bone sections may fracture already when the implant is inserted, which fracture may lead to the loss of the implant bed; the osteotomy technique is especially suitable in very unfavorable (narrow) jaw ridges, whereby the bone present is expanded in a substance-saving manner. This occurs especially in screw-type implants, since these implants are used as the osteotome themselves, unlike the cylindrical implants, and they are driven into the bone, rather than being screwed into the bone slowly partially by means of a machine and partially requiring a precut thread, especially in the case of bone that is thickened and hardened by means of the osteotomy technique.

The present invention also pertains to a process for creating openings in the jawbone for the implantation of implants by means of an oral surgical instrument (osteotome) comprising a holder, a shaft, and a working tip that has a circular cross section, whereby first a small opening is created in the jaw, especially in the upper jaw, by means of the preformer having a conical working tip by means of the lateral pushing away of the bone material of the jaw, which opening is still not sufficient to insert the implant to be implanted so that the bone material of the jaw, especially of the upper jaw, is then displaced by means of the implant bed former with a working tip that is adapted to the outer contour of the implant, whose diameter is somewhat greater than the largest diameter of the working tip of the preformer, to the extent that the opening created in the jaw is already adapted to the outer contour of the implant.

Finally, the present invention also pertains to the use of the oral surgical instrument (Osteotome) comprising a set of surgical instruments, which comprises at least one preformer having a conical working tip and at least one implant bed former having a working tip that is adapted to the outer contour of the implant, for creating openings in the jawbone for the implantation of implants.

The present invention is explained in detail below based on two different sets of dental instruments, each comprising a preformer having a conical working tip and an implant bed former adapted to the outer contour of the implant.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
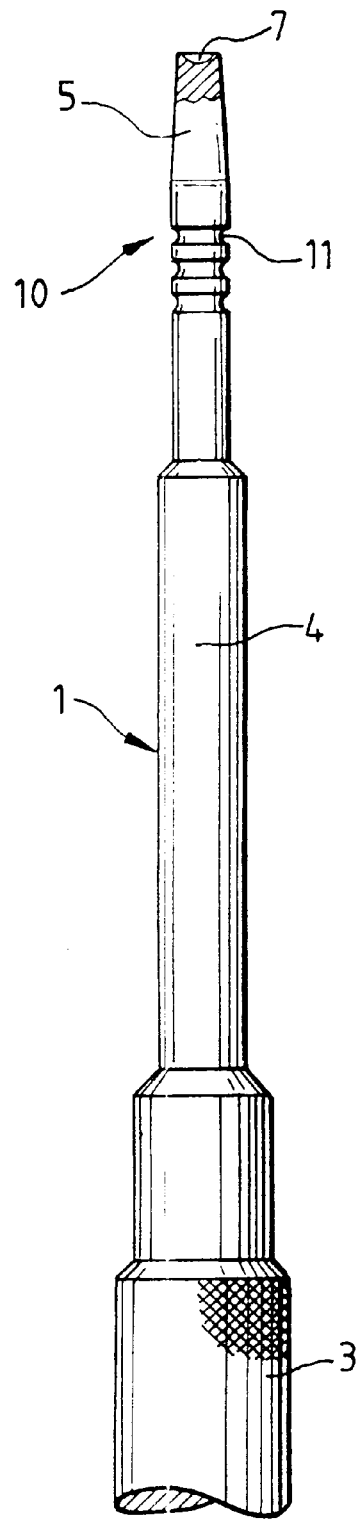
FIG. 1 is a side partially cutaway view of a preformer according to a first embodiment of the invention.
Figure 2:
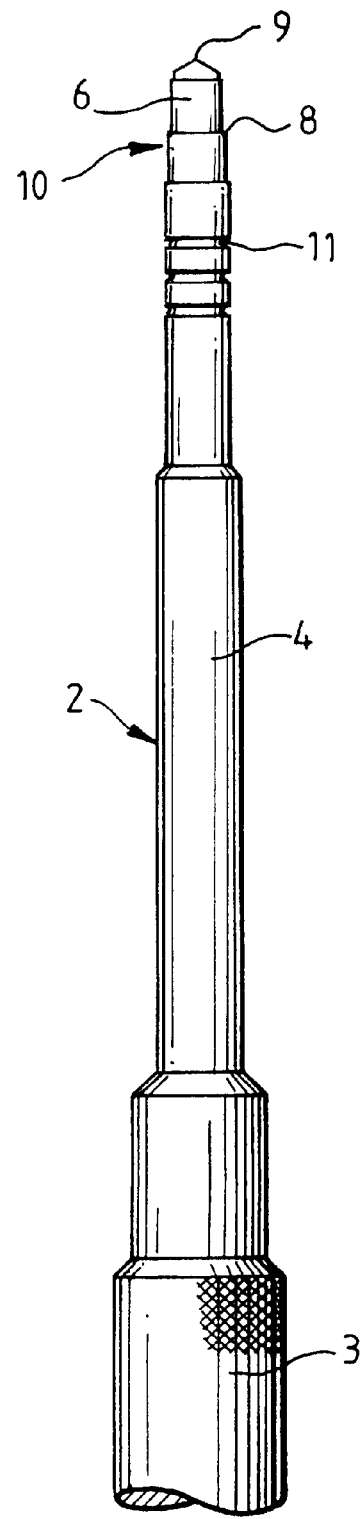
FIG. 2 is a side partially cutaway view of the implant bed former according to the first embodiment of the invention.

A set of oral surgical instruments (osteotome) for creating jaw openings for the implantation of implants (not shown) comprises in each case at least one preformer 1 according to FIG. 1 and one implant bed former 2, a so-called final former, according to FIG. 2. Each of these comprises a holder 3 as a handle with an axially and circumferentially knurled surface, a graduated shaft 4, which has a circular cross section and is connected to the holder, and a working tip 5 in the case of the preformer 1 and a working tip 6 in the case of the implant bed former 2. The preformer 1 and the implant bed former 2 are made of high-tensile, stainless-steel metallic material, especially V4A. The shaft 4, which connects the respective working tip 5, 6 with the respective holder 3, has multiple graduations in order to go from the diameter of 10 mm of the holder 3 via two graduations of 8 or 5 mm diameter to the diameters of the respective working tip 5, 6, which will still be described later. The holder 3 forming the handle, the shaft 4 and the working tips 5, 6 each have a circular cross section and are designed as one piece.

The working tip 5 of the preformer 1 according to FIG. 1 has a conical shape and has a concave spherical cap 7 on its front, distal end. The working tip 6 of the implant bed former 2 according to FIG. 2 has three graduations 8 in the direction of its end, each with smaller diameters, and a pointed-cone-shaped tip 9, whose cone angle is 118°. In this case, the graduations 8 are adapted to the graduations of a graduated cylinder or of a graduated screw as the implant, as will still be explained in detail later.

The shaft areas 10, which are connected directly to the working tips 5, 6 of the preformer 1 and the implant bed former 2, are each provided with at least one circumferential notch 11 as a depth scale. In each case, in the exemplary embodiment according to FIGS. 1 and 2, three notches are arranged at certain distances on the distal end of the preformer 1 and of the implant bed former 2.

Figure 3:
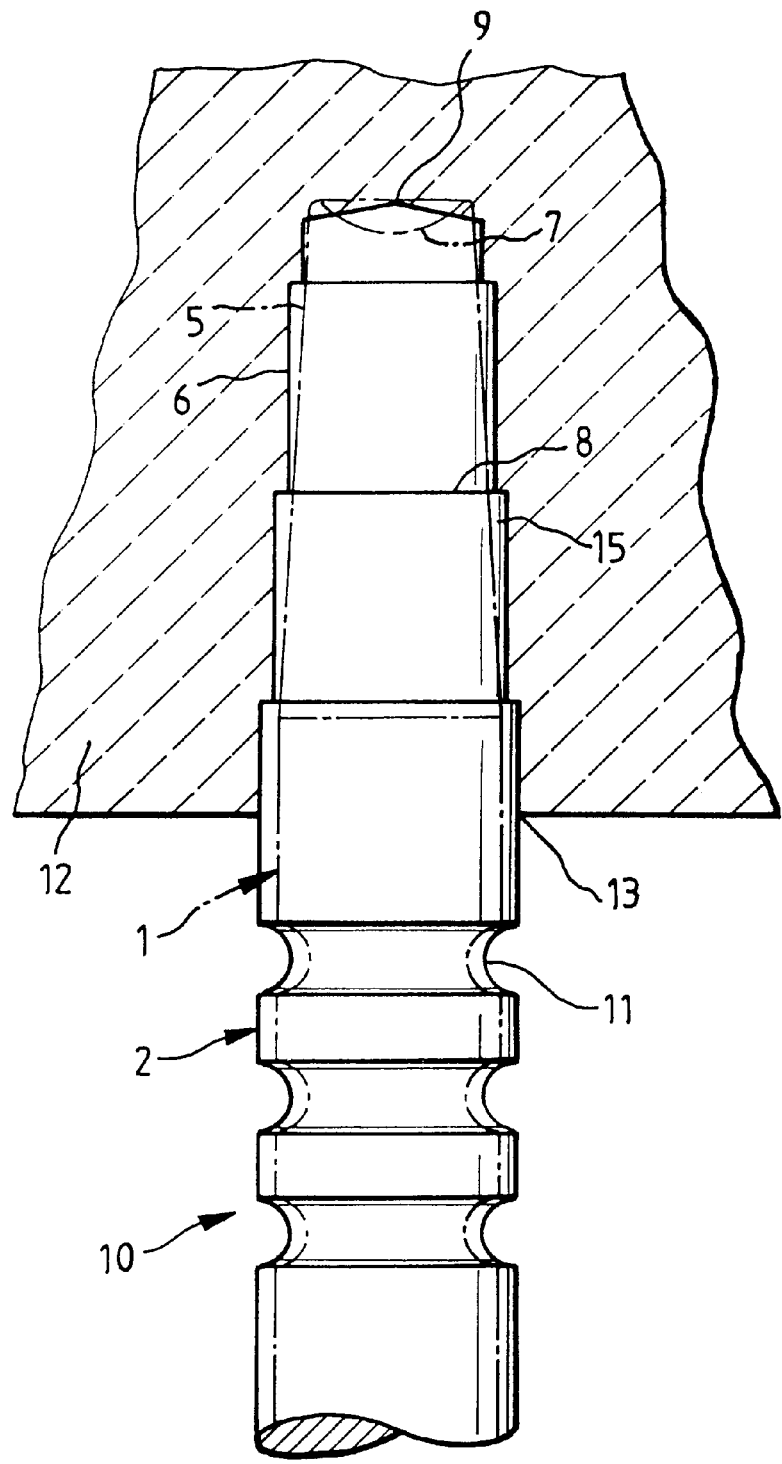
FIG. 3 is a side partially cutaway view of a working tip of the implant bed former according to FIG. 2 in the bone material of the upper jaw with representation of the contour lines of the associated preformer according to FIG. 1.

FIG. 3 shows a shaded view of the bone material of the upper jaw 12 of a patient, into which a jaw opening 13 is inserted, which is formed corresponding to the graduations 8 of the implant bed former 2. The implant bed former 2 is shown with bold lines in FIG. 3, whereas the contours of the preformer 1 are shown with fine lines in the implant bed former 2. This shows that the conical contour lines of the working tip of the preformer 1 run through the inner edges 14 of the graduations 8 of the graduated contour lines of the working tip 6 of the implant bed former 2, projecting onto the working tip 6 of the implant bed former 2. This shows that first a conical jaw opening is created in the upper jaw 12 by means of the working tip 5 of the preformer 1 (fine continuous lines), whereby a lens-shaped bone material is left behind based on the spherical cap 7 at the end of the preformer 1, which bone material is then displaced and is compressed when the implant bed former 2 penetrates through the tip 9. Each of the laterally projecting, triangular bone material areas 15, which are formed outside the contour line of the working tip 5 of the preformer (fine continuous lines) in the area of the graduations 8, are displaced during the penetration by means of the graduations 8 of the implant bed former 2.

FIG. 3 also shows the covering notches 11 of the preformer 1 and of the implant bed former 2, whereby the different inner diameters of the notches 11 are apparent based on the differences in diameter between the somewhat thinner preformer 1 and the somewhat thicker implant bed former 2. The notches 11 are used by the dentist to position the respective dental instrument, the preformer 1 or the implant bed former 2, with the highest precision in the depth of the bone material of the upper jaw 12.

Figure 4:
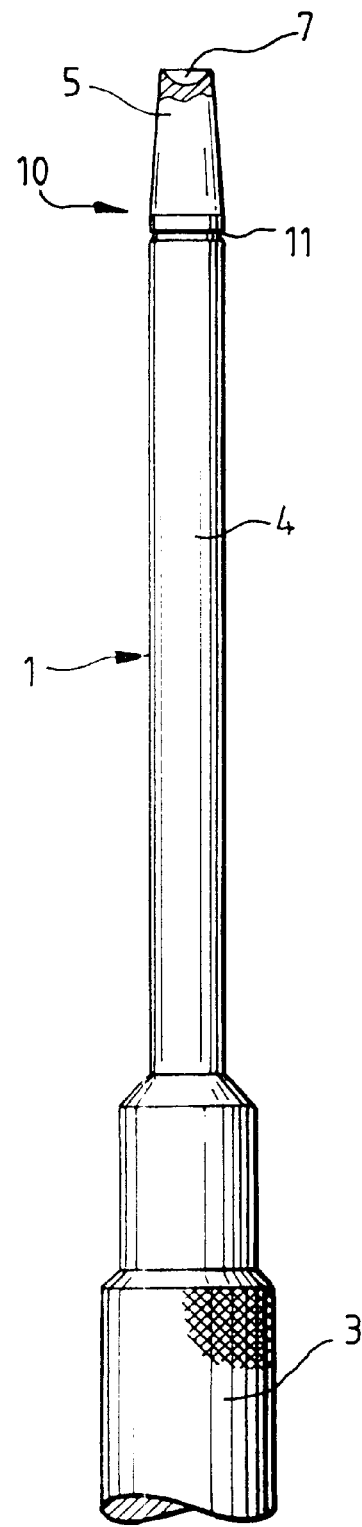
FIGS. 4 and 6 are side partially cutaway views of the preformer according to FIG. 1 with different dimensions.
Figure 5:
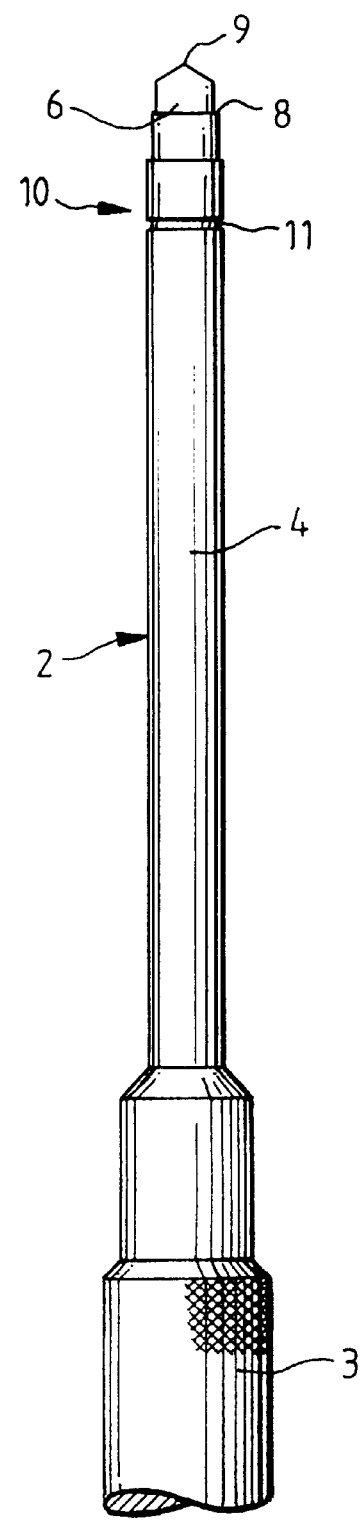
FIGS. 5 and 7 are side partially cutaway views of the implant bed formers, which belong to the preformers according to FIGS. 4 and 6, respectively.
Figure 6:
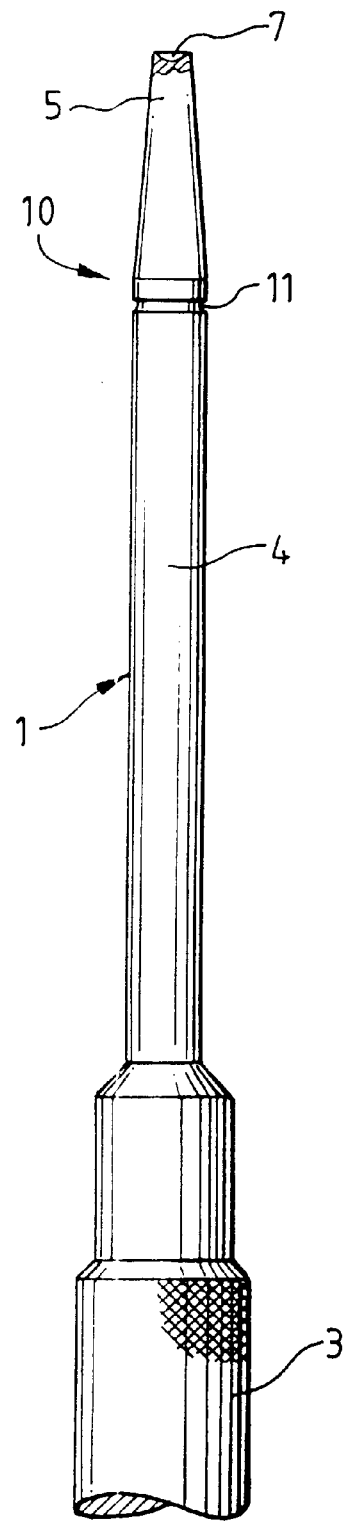
Figure 7:
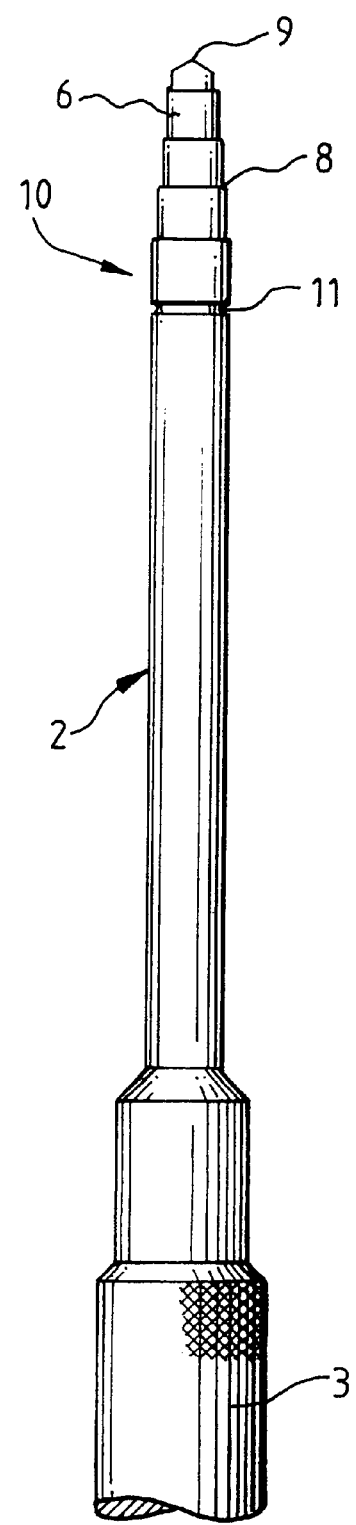

FIGS. 4 and 6 show modified preformers 1 having different dimensions of the working tips 5 and each having only one notch 11. The associated implant bed formers 2 are shown in FIGS. 5 and 7, respectively. It should be noted that the implant bed former 2 according to the embodiment in FIG. 7 has four graduations 8, whereas the implant bed former 2 according to FIGS. 2 and 5 only have three graduations 8 each.

The set of oral surgical instruments (osteotome) according to FIGS. 1 to 7 are used for the implantation of Frialit-2 graduated cylinders or graduated screws, i.e., graduated implants with and without outer threads. In an implant with an outer thread, the respective inner diameter of the thread is used as an indicator for the graduations 8 of the implant bed former 2.

A set of instruments of this embodiment has the following dimensions:

| Preformer 1 (mm) | Implant bed former 2 | Graduated diameter (mm) | Graduation (mm) |
| --- | --- | --- | --- |
| 3.3; 2.5 | 3.8 | 2.6; 3.0; 3.4 | 11; 13; 15 |
| 4.4; 3.0 | 4.5 | 3.5; 4.0 | 10 |
| 4.4; 2.4 | 4.5 | 3.5; 4.0 | 13 |
| 4.4; 2.2 | 4.5 | 3.0; 3.5; 4.0 | 15 |
| 5.4; 3.4 | 5.5 | 4.2; 4.8 | 10 |
| 5.4; 2.9 | 5.5 | 3.6; 4.2; 4.8 | 13 |
| 5.4; 2.5 | 5.5 | 3.0; 3.5; 4.2; 4.8 | 15 |
| 6.0; 3.85 | 6.5 | 4.6; 5.2; 5.8 | 13 |
| 6.0; 3.85 | 6.5 | 4.6; 5.2; 5.8 | 15 |

Figure 9:
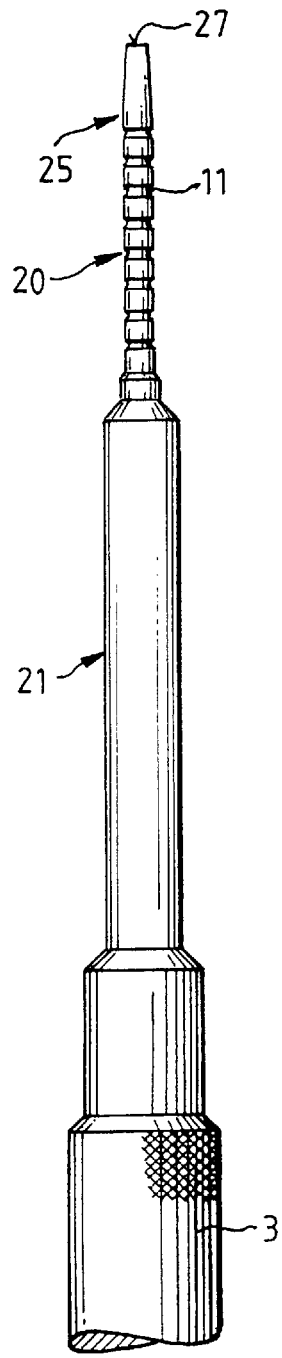
Figure 10:
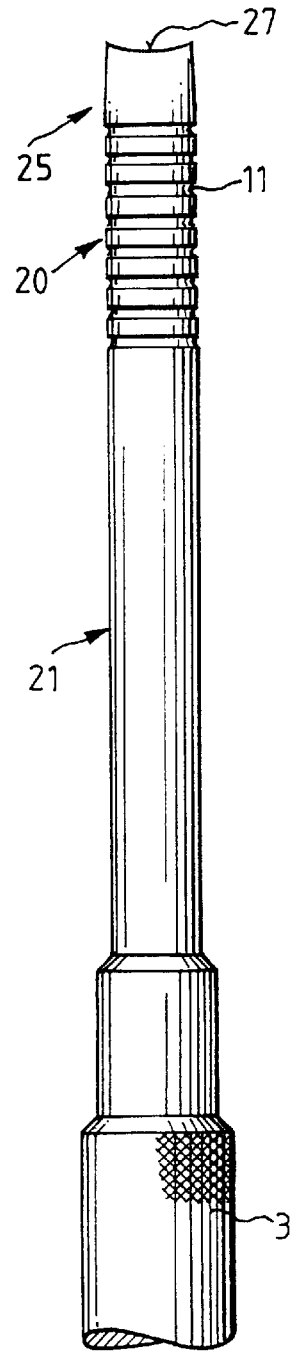
Figure 11:
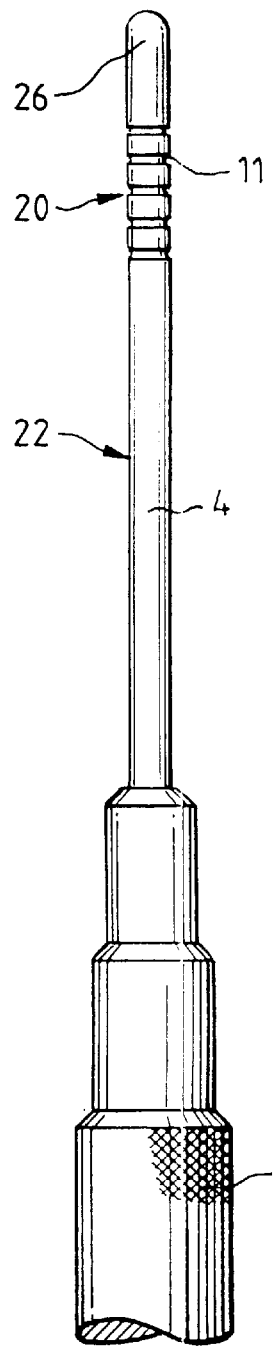
FIGS. 11 through 13 are side partially cutaway views of the implant bed former according to the second embodiment.
Figure 12:
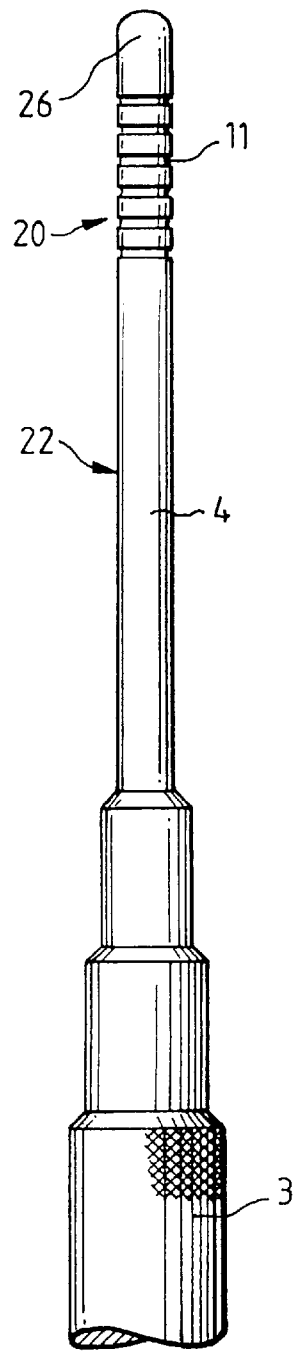
Figure 13:
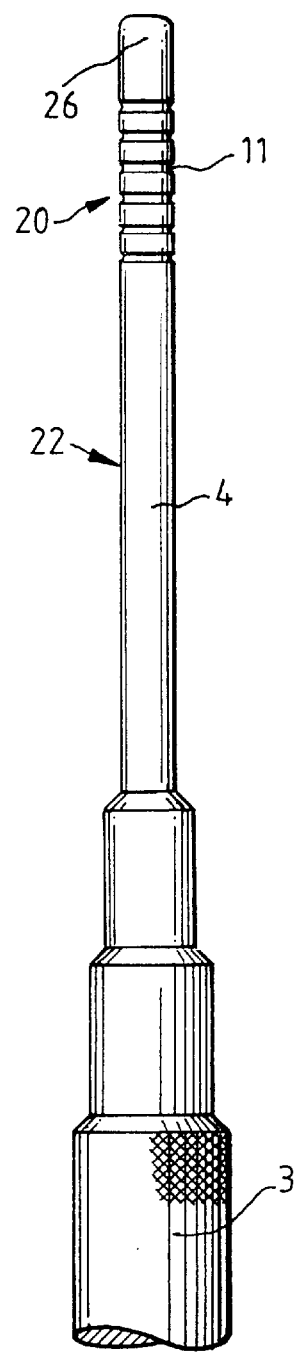

The second embodiment of oral surgical instruments (osteotome) shown in FIGS. 8 through 13 shows a set of ten preformers 21 (FIGS. 8 through 10), beginning with a working tip 25 having a tip diameter of 1 mm, and three implant bed formers 22 (FIGS. 11 through 13).

Figure 8:
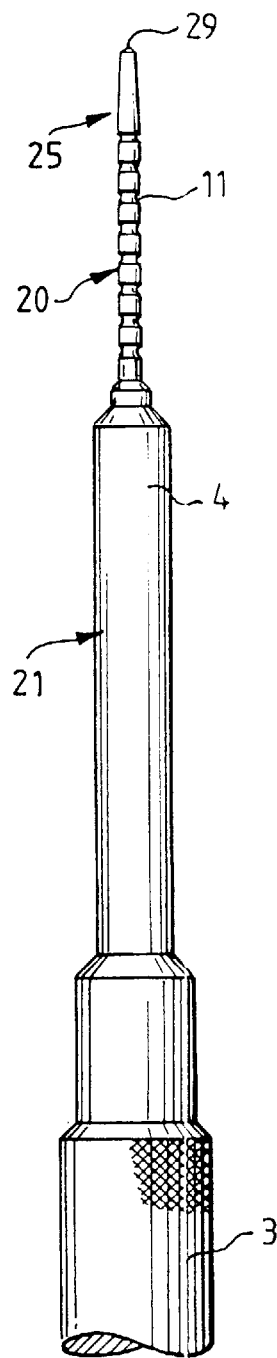
FIGS. 8 through 10 are side partially cutaway views of the preformer according to a second embodiment.

The working tip 25 of the preformer 21 according to FIG. 8 has a conical shape and a pointed-cone-shaped tip 29 on its end with a cone angle of 118° and a diameter of 1 mm. This working tip 25 has a conically expanding shaft with a diameter of 1.5 mm. All other preformers of this set have a concave spherical cap 27 on their free end and expand their diameters only by 0.5 mm. This set of preformer 21 instruments is used for the universal (pre-) expansion of the bone for the common implant sizes.

The shaft area 20 connected to the working tip 25 has a graduated shape with eight notches 11 with various distances from the tip 29. The preformers 21 of varying diameters shown in FIGS. 9 and 10 have corresponding notches 11 at the same distances as in the preformer 21 according to FIG. 8. The working tip 25 is provided with a conical outer contour, whose cone angle is somewhat greater than the cone angle of the working tip 25 of the preformer 21 according to FIG. 8 with the tip 29. Moreover, the end of the preformers 21 according to FIGS. 9 and 10 is provided with a concave spherical cap 27. The set of instruments (osteotome) of the second embodiment shown in FIGS. 8 through 10 is used to form and expand the jaw openings up to a diameter of 6 mm for the subsequent creation of openings by means of the implant bed formers 22 according to FIGS. 11 through 13. The dimensions of the preformers 21 are:

| | |
| --- | --- |
| Preformer 21 (with Tip) | 1.5 mm; 1.0 mm |
| Preformer 21 (with spherical cap) | 2.0 mm; 1.5 mm |
| | 2.5 mm; 2.0 mm |
| | 3.0 mm; 2.5 mm |
| | 3.5 mm; 3.0 mm |
| | 4.0 mm; 3.5 mm |
| | 4.5 mm; 4.0 mm |
| | 5.0 mm; 4.5 mm |
| | 5.5 mm; 5.0 mm |
| | 6.0 mm; 5.5 mm |

The length of the conical working tips 25 is 6.0 mm in each case.

The eight notches 11 have distances of 6.0 mm to 20.0 mm from the end.

The implant bed formers 22 of the second embodiment of the set of oral surgical instruments (osteotome) shown in FIGS. 11 and 13 comprise three implant bed formers 22 having cylindrical working tips and circular or flat, rounded ends, as well as a number of notches 11 for the formation of graduations. The implant bed formers 22 are used for the implantation of cylindrical implants without threads or with partial or completely continuous threads. The dimensions of the cylindrical implant bed formers 22 of the model ITI-Stramann-Bonefit are:

diameter of the working tips 2.7 mm or 3.5 mm,
length of the working tips 6.0 mm or 8.0 mm.

The five or six notches 11 have distances of 6.0 mm or 8.0 mm from the working end.

While specific embodiments of the invention have been shown and described in detail to illustrate the application of the principles of the invention, it will be understood that the invention may be embodied otherwise without departing from such principles.

What is claimed is:

1. A set of oral surgical instruments (osteotome) for creating openings in the jawbone for the implantation of implants, comprising:

a preformer surgical instrument having a conical working tip with a working tip diameter;

an implant bed former surgical instrument having a working tip adapted to an outer contour of said implant, said implant bed former having a working tip largest diameter, said working tip diameter of said preformer being smaller than said working tip largest diameter of said implant bed former, each said surgical instrument including a holder, a shaft and a working tip that has a circular cross section.

2. The instrument in accordance with claim 1, wherein said working tip of said implant bed former is for forming a jaw opening for the implant having a graduated diameter has an outer contour having a graduated diameter on a free end.

3. The instrument in accordance with claim 1, wherein said working tip of said preformer includes conical contour lines which run through inner edges of graduations of graduated contour lines of said working tip of said implant bed former projecting onto said working tip of said implant bed former.

4. The instrument in accordance with claim 3, wherein a front end of said working tip of said preformer is provided with a concave spherical cap.

5. The instrument in accordance with claim 3, wherein a front end of said working tip of said implant bed former is shaped like a pointed cone having a tip.

6. The instrument in accordance with claim 5, wherein a cone angle of said tip is about 120°.

7. The instrument in accordance with claim 1, wherein a plurality of said preformers are provided and a front end of said working tip of one said preformer with a smallest diameter is shaped with a pointed-cone-shaped tip.

8. The instrument in accordance with claim 7, wherein said cone angle of said tip is about 120°.

9. The instrument in accordance with claim 1, wherein a plurality of said prefomers are provided and a front end of said working tip of a preformer having a larger diameter is provided with a concave spherical cap.

10. The instrument in accordance with claim 1, wherein a shaft area directly connected to said working tip of said preformer is provided with at least one circumferential notch as a depth scale and a shaft area directly connected to said working tip of said implant bed former is provided with at least one circumferential notch as a depth scale.

11. The instrument in accordance with claim 10, wherein said shaft area of said preformer has a plurality of said notches arranged at a distance from one another as a depth scale and said shaft area of said implant bed former has a plurality of said notches arranged at a distance from one another as a depth scale.

12. The instrument in accordance with claim 1, wherein:

said working tips of said preformer and said former have a substantially even outer surface in a circumferential direction.

13. The instrument in accordance with claim 1, wherein:

said working tips of said preformer and said former have a substantially smooth outer surface in a circumferential direction.

14. The instrument in accordance with claim 1, wherein:

said working tips of said preformer and said former have a substantially symmetrical outer surface about a longitudinal axis of respective said preformer and former.

15. The instrument in accordance with claim 1, wherein:

said working tip of said preformer has means for substantially symmetrically and laterally forcing bone material away from a longitudinal axis of said preformer when said preformer is inserted into the jawbone.

16. A process for creating openings in the jawbone for the implantation of implants by means of an oral surgical instrument (osteotome) comprising a holder, a shaft, and a working tip having a circular cross section, the process comprising the steps of:

creating a first small opening in the jaw by means of a preformer having a conical working tip by lateral pushing away of bone material of the jaw and displacing bone material of the jaw with at least one implant bed former having a working tip that is adapted to an outer contour of the implant such that an opening created in the jaw is adapted to the outer contour of the implant.

17. A process in accordance with claim 16, wherein:

said lateral pushing away is in a direction radially away from a longitudinal axis of said working tip of said preformer.

18. A process for using an oral surgical instrument (osteotome) set, the process comprising:

using at least one preformer having a conical working tip; and using at least one implant bed former having a working tip that is adapted to the outer contour of the implant for creating openings in the jawbone for the implantation of implants, said working tip of said preformer having a substantially circular cross section and said working tip of said former having a substantially circular cross section.

19. A process for using an oral surgical instrument (osteotome) set, the process comprising:

using at least one preformer having a conical working tip, including substantially symmetrically and radially forcing bone material away from a longitudinal axis of said preformer when said preformer is inserted into the jawbone; and using at least one implant bed former having a working tip that is adapted to the outer contour of the implant for creating openings in the jawbone for the implantation of implants.

* * * * *